(12) United States Patent
Ishida (10) Patent No.: US 8,365,740 B1
(45) Date of Patent: Feb. 5, 2013

(54) METHODS AND APPARATUS FOR RESTRAINING A PERSON

(76) Inventor: Keith Ishida, Ontario, OR (US)

( * ) Notice: Subject to any disclaimer, the term of this patent is extended or adjusted under 35 U.S.C. 154(b) by 400 days.

(21) Appl. No.: 12/661,034

(22) Filed: Mar. 9, 2010

Related U.S. Application Data (60) Provisional application No. 61/209,717, filed on Mar. 10, 2009.

(51) Int. Cl.
*A61F 5/37* (2006.01)
(52) U.S. Cl. ............................ 128/870; 128/869; 5/628
(58) Field of Classification Search .................. 128/845, 128/849, 869, 870, 871, 872; 602/32, 33, 602/34, 35; 54/79.1, 79.2; 5/494, 621, 623, 5/628; 224/158, 250; 280/18
See application file for complete search history.

(56) References Cited

U.S. PATENT DOCUMENTS

| | | | | |
|---|---|---|---|---|
| 4,979,520 A * | 12/1990 | Boone et al. | ................... | 128/870 |
| 5,150,487 A * | 9/1992 | Hemphill | ........................... | 5/625 |
| 6,135,114 A * | 10/2000 | Elliott et al. | ................... | 128/869 |
| 6,477,728 B1 * | 11/2002 | Faz | ................................... | 5/625 |
| 6,568,009 B2 * | 5/2003 | Linger et al. | ...................... | 5/627 |

\* cited by examiner

*Primary Examiner* — Justine Yu
*Assistant Examiner* — Raymond E Harris

(57) ABSTRACT

A patient restraining device is secured to a patient supporting structure to more safely support a person's body during transport from one place to another. The device includes a sheet of fabric and connector straps secured to the fabric. After the device is fastened to the patient supporting structure, and the person is positioned on the patient supporting structure, the fabric is wrapped about the person's body, and the connector straps are secured about the fabric and the person's body. Among other things, the device may be used to increase the "patient capacity" of an otherwise conventional ambulance cot.

21 Claims, 6 Drawing Sheets

Fig. 9

METHODS AND APPARATUS FOR RESTRAINING A PERSON

CROSS-REFERENCE TO RELATED APPLICATION

Disclosed herein is subject matter that is entitled to the filing date of U.S. Provisional Application No. 61/209,717, filed Mar. 10, 2009.

FIELD OF THE INVENTION

The present invention relates to methods and apparatus for restraining a person, and in a preferred application, to patient restraining devices.

BACKGROUND OF THE INVENTION

On various occasions and in various situations, a need exists to transport a person by ambulance cot, stretcher, or other such devices. For the most part, these devices have been built according to generally accepted standards, taking into account factors that include the size of the people to be transported.

In recent times, people are increasingly becoming obese, and more obese than ever. At some point, obese people reach a size that makes it dangerous, for both them and the people doing the transporting, for them to be transported by traditional means. In other words, most of the currently existing ambulance cots, stretches, etc. are not large enough to accommodate a growing segment of the population.

One possible solution to this problem is to introduce larger ambulance cots, but this solution would not be simple or cost effective to implement. For example, larger ambulance cots may not fit into existing ambulances, or may not fit through existing doorways. Also, replacing all existing ambulance cots would be expensive and take time.

Another possible solution to this problem is to provide a supplement platform that essentially rests on top of a traditional ambulance cot. However, this solution would encounter problems similar to those discussed above with respect to introducing larger ambulance cots.

In other words, there exists a need for a practical solution to transporting people that are too big for existing patient supporting structures.

SUMMARY OF THE INVENTION

The present invention provides methods and apparatus for restraining a person relative to a patient supporting structure. On a preferred embodiment, the device includes a sheet of fabric and connector straps secured to the fabric. After the device is fastened to the patient supporting structure, and the person is positioned on the patient supporting structure, the fabric is wrapped about the person's body, and the connector straps are secured about the fabric and the person's body. In a preferred application, the device is secured to an ambulance cot to accommodate people that would not otherwise fit safely onto the cot. Many features and/or advantages of the present invention will become apparent from the more detailed description that follows.

BRIEF DESCRIPTION OF THE FIGURES OF THE DRAWING

With reference to the Figures of the Drawing, wherein like numerals represent like parts and assemblies throughout the several views.

DETAILED DESCRIPTION OF A PREFERRED EMBODIMENT

Figure 1:
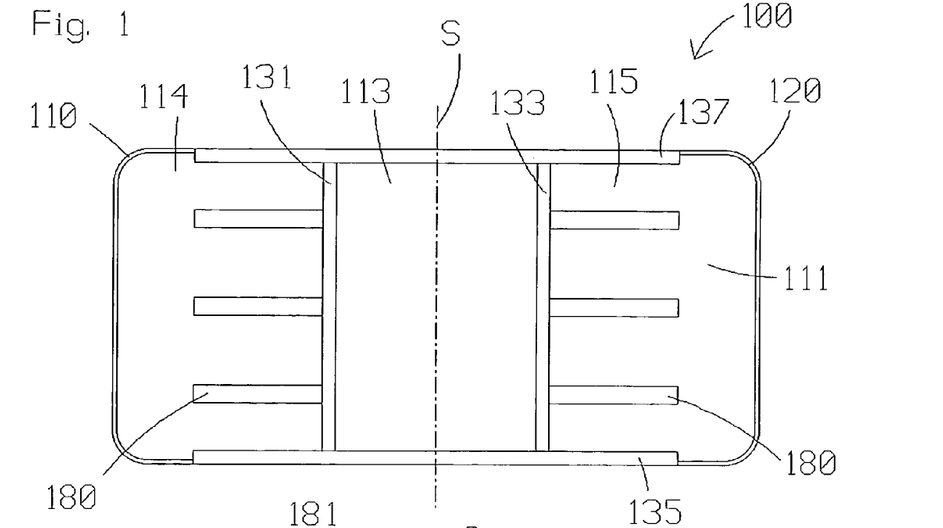
FIG. 1 shows an interior side of a patient restraining device constructed according to the principles of the present invention.
Figure 2:
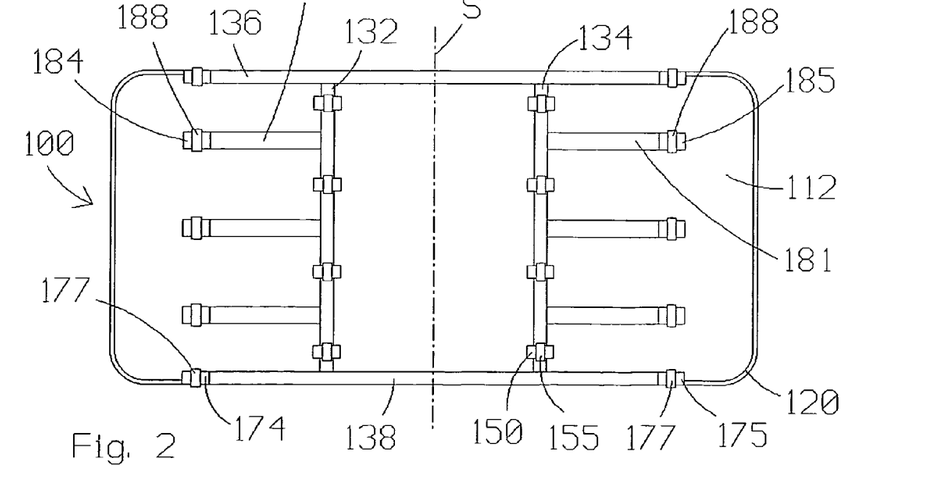
FIG. 2 shows an opposite, exterior side of the patient restraining device of FIG. 1.

FIGS. 1-2 show a patient restraining device 100 constructed according to the principles of the present invention, and useful for temporarily, safely, and comfortably limiting movement of a body portion of a human patient relative to a patient supporting structure. Generally speaking, the device 100 includes a sheet of fabric 110, reinforcing straps 131-138 secured to the fabric 110, anchor straps 150 secured to the reinforcing straps 131 and 132, and patient restraining straps 174, 175 and 184, 185 secured to the reinforcing straps 131-138.

The fabric 110 is preferably a sheet of Phifertex mesh that measures three feet in width and six feet in length. Although this size is considered preferable, persons skilled in the art will recognize that alternative embodiments may be made of different sizes. Accordingly, the invention may alternatively be described in terms of size ranges, including, for example, two feet to four feet in width and five feet to seven feet in length. Also, the size may be described in terms of minimums, including, for example, at least two feet wide and at least five feet long.

The mesh comprises longitudinally extending elements that are spaced one-sixteenth of an inch apart from one another, and laterally extending elements that are spaced one-eighth of an inch apart from one another. An advantage of the mesh is that it does not fully encapsulate a person's body, and it allows someone to see through the fabric 110 and thereby continue monitoring conditions of the person's body (e.g. bleeding). Additional advantages of using a fabric such as Phifertex are that the material is durable, flexible, inelastic, washable and reusable. Although Phifertex mesh is the preferred material, persons skilled in the art will recognize that alternative embodiments of the present invention may be made with other known suitable materials.

Each of the four corners of the fabric sheet 110 is rounded at a radius of 4 inches. A trim element 120 is secured about the perimeter of the fabric sheet 110, so there are no exposed edges of the sheet 110. The trim element 120 is preferably a one-inch wide strip of rugged cloth that is folded in half over the edge of the fabric 110, and sewn to itself with the fabric 110 retained therebetween.

The first reinforcing strap 131 and the second reinforcing strap 132 are disposed on respective first and second sides 111 and 112 of the sheet 110. The straps 131 and 132 are aligned with one another to extend laterally across the sheet 110, and the first strap 131 is sewn to the second strap 132 with the sheet 110 secured therebetween. Similarly, the third reinforcing strap 133 and the fourth reinforcing strap 134 are disposed on respective first and second sides 111 and 112 of the sheet 110. The straps 133 and 134 are aligned with one another to extend laterally across the sheet 110, and the third strap 133 is sewn to the fourth strap 134 with the sheet 110 secured therebetween.

The straps 131 and 132 cooperate with the straps 133 and 134 to divide the sheet into three sections, including a middle section 113, a first end section 114, and an opposite, second end section 115. Each section 113-115 measures three feet in width (top to bottom in FIGS. 1-2) and two feet in length (side to side in FIGS. 1-2). The middle section 113 is sized and configured to overlie an upwardly facing body supporting surface on an ambulance cot, as further described below.

The fifth reinforcing strap 135 and the sixth reinforcing strap 136 are disposed on respective first and second sides 111 and 112 of the sheet 110. The straps 135 and 136 are aligned with one another to extend longitudinally along a side edge of the sheet 110, and the fifth strap 135 is sewn to the sixth strap 136 with the sheet 110 and the trim member 120 secured therebetween. Similarly, the seventh reinforcing strap 137 and the eighth reinforcing strap 138 are disposed on respective first and second sides 111 and 112 of the sheet 110. The straps 137 and 138 are aligned with one another to extend longitudinally along an opposite side edge of the sheet 110, and the seventh strap 137 is sewn to the eighth strap 138 with the sheet 110 and the trim member 120 secured therebetween.

All of the reinforcing straps 131-138 are preferably one and one-half inch wide Nylon webbing. However, persons skilled in the art will recognize that other sizes and/or types of straps may be used on alternative embodiments without departing from the scope of the present invention. Also, the reinforcing straps 131-138 may be secured in placing using additional or alternative means, including adhesives, bonding agents, or rivets or other fasteners, for example. On the preferred embodiment, the reinforcing straps 131-138 are glued in place relative to one another, and then sewn in place.

Eight anchor straps or fasteners 150 are disposed on the second side or exterior side 112 of the sheet of fabric 110. Each anchor strap 150 is preferably a one and one-half inch wide strap of Nylon webbing. Four of the anchor straps 150 are sewn in place between the overlapping reinforcing straps 131 and 132, and four more of the anchor straps 150 are sewn in place between the overlapping reinforcing straps 133 and 134. As noted above with reference to the reinforcing straps 131-138, different sizes and/or types of straps may be used on alternative embodiments, and/or the straps 150 may be fastened in place by additional or alternative means. The outboard anchor straps 150 are disposed three inches inward from the edge of the sheet of fabric 110, and eight inches separates adjacent anchor straps 150 along either reinforcing strap 132 or 134.

Figure 3:
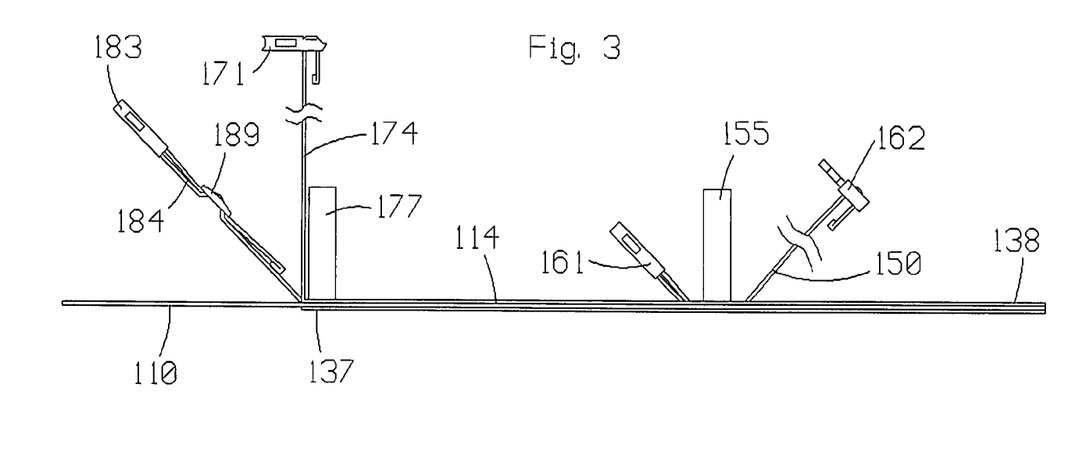
FIG. 3 is a side view of one end of the patient restraining device of FIG. 1.
Figure 4:
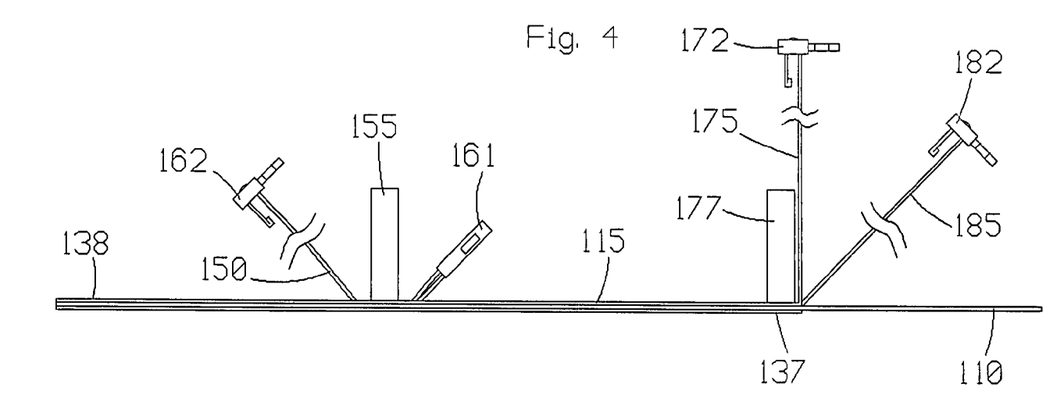
FIG. 4 is a side view of an opposite end of the patient restraining device of FIG. 1.

As shown in FIGS. 3-4, a first end of each anchor strap 150 is inserted through a female buckle member 161 and then secured in place together with an adjacent segment of the strap 150. As a result, the female buckle member 161 is captured on a looped portion of the strap 150 proximate a respective reinforcing strap 132 or 134. An opposite, second end of each anchor strap 150 is inserted through a male buckle member 162 and then doubled onto itself to prevent removal from the male buckle member 162. As a result, the male buckle member 162 is selectively slidable along the second end of the anchor strap 150 to adjust the operational length of the strap 150. The second end of each anchor strap 150 extends twenty inches when fully deployed in a longitudinal direction. The buckle members 161 and 162 are conventional parts that snap into and out of engagement with one another to selectively interconnect the opposite ends of the anchor strap 150.

A separate lashing strap 155 is preferably provided for each anchor strap 150. Each lashing strap 155 has a middle portion that is secured to respective reinforcing strap 132 or 134 at a point of intersection with a respective anchor strap 150. Each lashing strap 155 includes a first distal end that is provided with loop-type fasteners and an opposite, second distal end that is provided with hook-type fasteners that face toward the loop-type fasteners when the ends of the strap 155 overlap. Each lashing strap 155 releasably secures a respective anchor strap 150 in a folded storage configuration (as shown in FIG. 2). The ends of the lashing strap 155 are separated from one another to free the associated anchor strap 150 for deployment and use, as further described below.

First and second patient restraining straps or connectors 174 and 175 are connected to opposite, first and second ends of the reinforcement strap 136. Similarly, third and fourth patient restraining straps or connectors 174 and 175 are connected to opposite, first and second ends of the reinforcement strap 138. On the preferred embodiment 100, the patient restraining straps 174 and 175 are integral extensions of respective reinforcement straps 136 and 138. Each patient restraining strap 174 or 175 may be described in terms of (1) a first portion that is secured to the sheet of fabric 110 like the reinforcing straps 136 and 138, and a second portion that is a loose end; or alternatively, (2) just loose portions that are secured to respective distal ends of respective reinforcing straps 136 and 138.

As shown in FIG. 3, respective distal ends of the first and third patient restraining straps 174 are inserted through respective female buckle members 171 and then doubled onto themselves to prevent removal from the female buckle members 171. As a result, the female buckle members 171 are selectively slidable along respective first and third patient restraining straps 174 to adjust the operational length of the straps 174. As shown in FIG. 4, respective distal ends of the second and fourth patient restraining straps 175 are inserted through respective male buckle members 172 and then doubled onto themselves to prevent removal from the male buckle members 172. As a result, the male buckle members 172 are selectively slidable along respective second and fourth patient restraining straps 175 to adjust the operational length of the straps 175. The buckle members 171 and 172 are conventional parts that snap into and out of engagement with one another to selectively interconnect the opposing first and second patient restraining straps 174 and 175, and the opposing third and fourth patient restraining straps 174 and 175.

A separate lashing strap 177 is preferably provided for each patient restraining strap 174 and 175. Each lashing strap 177 is identical in form and function to the lashing straps 155. Each lashing strap 177 releasably secures a respective patient restraining strap 174 or 175 in a folded storage configuration (as shown in FIG. 2). The ends of the lashing strap 177 are separated from one another to free the associated patient restraining strap 174 or 175 for deployment and use, as further described below. When fully deployed in a longitudinal direction each patent restraining strap 174 or 175 extends twenty inches beyond a respective end of the sheet of fabric 110. This extent of deployment may alternatively be described as at least twelve inches.

Three patient restraining straps or connectors 184 are connected to the first end section 114 of the sheet of fabric 100. Similarly, three patient restraining straps or connectors 185 are connected to the second end section 115 of the sheet of fabric 110. Each patient restraining strap 184 and 185 may be described in terms of (1) a first portion that, together with a corresponding, opposite side strap 180, is secured to the sheet of fabric 110 like the reinforcing straps 131-138, and a second portion that is a loose end; or alternatively, (2) just loose portions that are connected to the distal ends of respective reinforcing straps 181. In any event, each reinforcing strap 180 has a first end that is retained between respective reinforcing straps 131-134, and extends longitudinally one foot from respective reinforcing straps 131-134 to an opposite, second end. Six inches separates each reinforcing strap 180 from an adjacent reinforcing strap 135-138, and eight inches separates adjacent reinforcing straps 180 from one another.

As shown in FIG. 3, respective distal ends of the patient restraining straps 184 are inserted through respective slides 189, then through respective female buckle members 183, then back through respective slides 189, and are then doubled onto themselves to prevent removal from the slides 189. As a result, the female buckle members 183 are selectively adjustable along respective patient restraining straps 184 to adjust the operational length of the straps 184. As shown in FIG. 4, respective distal ends of the patient restraining straps 185 are inserted through respective male buckle members 182 and then doubled onto themselves to prevent removal from the male buckle members 182. As a result, the male buckle members 182 are selectively slidable along respective patient restraining straps 185 to adjust the operational length of the straps 185. The buckle members 183 and 182 are conventional parts that snap into and out of engagement with one another to selectively interconnect the opposing patient restraining straps 184 and 185.

As shown in FIG. 2, a separate lashing strap 188 is preferably provided for each patient restraining strap 184 and 185. Each lashing strap 188 is identical in form and function to the lashing straps 155. Each lashing strap 188 releasably secures a respective patient restraining strap 184 or 185 in a folded storage configuration (as shown in FIG. 2). The ends of the lashing strap 188 are separated from one another to free the associated patient restraining strap 184 or 185 for deployment and use, as further described below. When fully deployed in a longitudinal direction each patent restraining strap 184 and 185 extends twenty inches beyond a respective end of the sheet of fabric 110. This extent of deployment may alternatively be described as at least twelve inches.

On alternative embodiments of the invention, the disclosed buckle members may be replaced by alternative arrangements. For example, different types of conventional buckles, clasps, fasteners, hooks, latches and the like may be substituted for the disclosed buckle members. Alternatively, a belt buckle may be provided on one strap and maneuvered into engagement with any of a series of holes formed at longitudinal intervals in an opposing strap. Also, hook-and-loop fasteners may be disposed on the straps and/or the fabric to releasably secure the straps in place.

Figure 9:
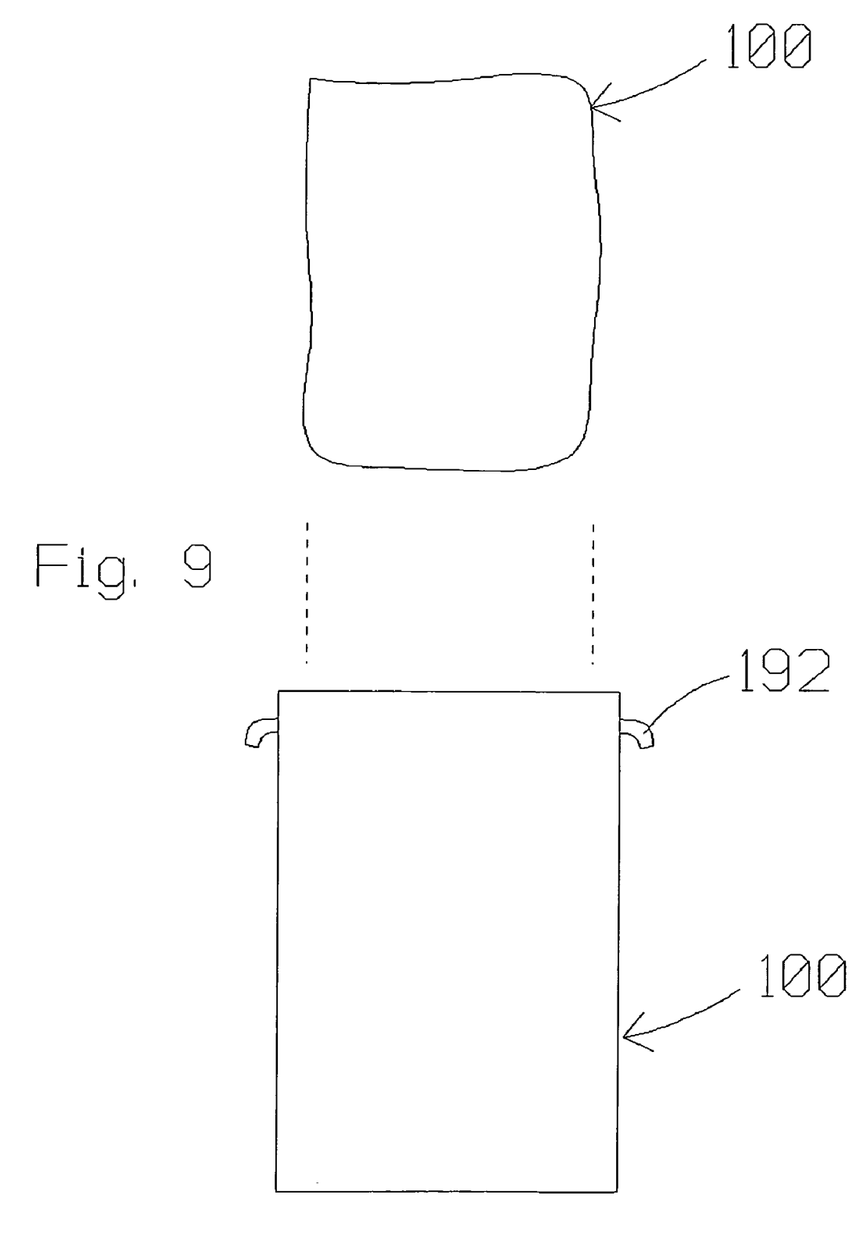
FIG. 9 is a diagrammatic front view of the patient restraining device of FIG. 1 folded into a compact configuration and shown in relation to a storage bag.

FIG. 9 is a diagrammatical representation of the device 100 in a folded configuration that measures less than eighteen inches vertically (top to bottom in FIG. 9), less than twelve inches horizontally (side to side in FIG. 9), and less than six inches thick (perpendicular to the drawing sheet of FIG. 9). When so configured, the device 100 occupies less than one cubic foot of space and fits into an appropriately sized bag 190 having an open upper end, and a drawstring 192 capable of cinching the upper end into a relative closed configuration. The bag 190 is preferably made from Nylon ripstock material, and keeps the device 100 clean and in a relatively convenient configuration for storage and transport.

Figure 5:
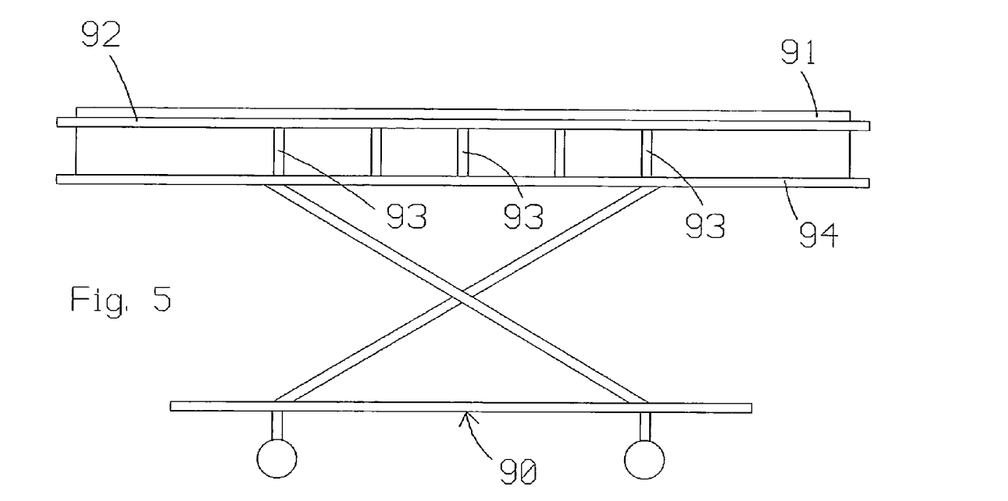
FIG. 5 is a side view of an ambulance cot.
Figure 6:
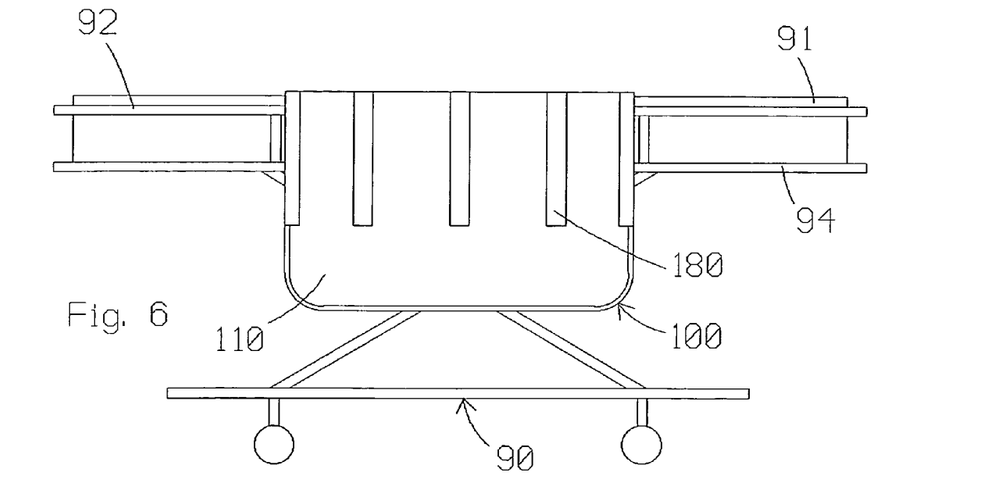
FIG. 6 is a side view of the patient restraining device of FIG. 1 secured in place on top of the ambulance cot of FIG. 5.

FIG. 5 is a diagrammatic representation of a conventional ambulance cot 90. The cot 90 may be described as a patient supporting structure having a body supporting platform 91. The platform 91 has a length that is measured from a head end to a foot end (left to right in FIG. 5), and a width that is measured laterally from a left side to a right side (perpendicular to the drawing sheet of FIG. 5). Left and right rails 92 are disposed along respective left and right sides of the platform 91. Posts 93 are interconnected between respective rails 92 and a relatively lower base structure 94. The rails 92, posts 93 and base structure 94 cooperate to define a mattress frame or support structure.

Figure 7:
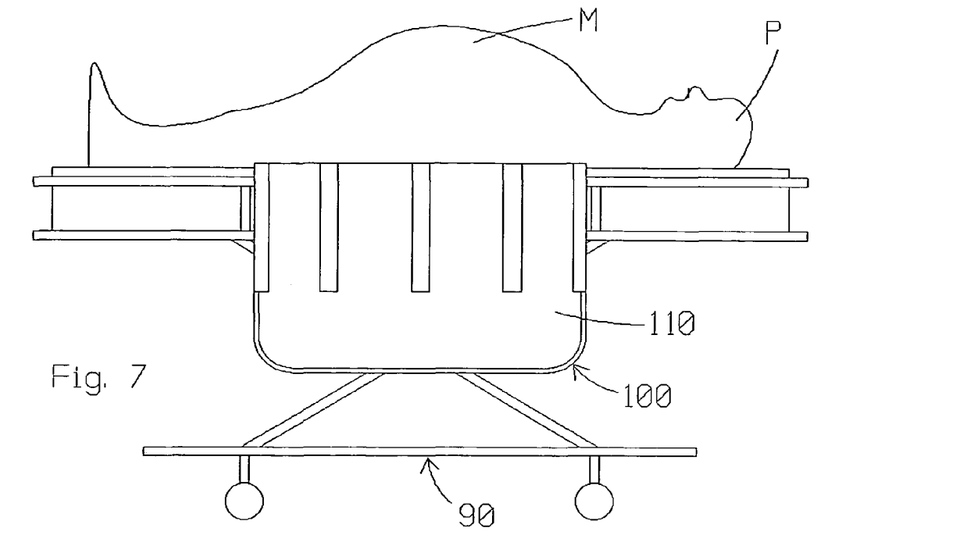
FIG. 7 is a side view of a bariatric person lying supine on top of the patient restraining device and ambulance cot of FIG. 6.
Figure 8:
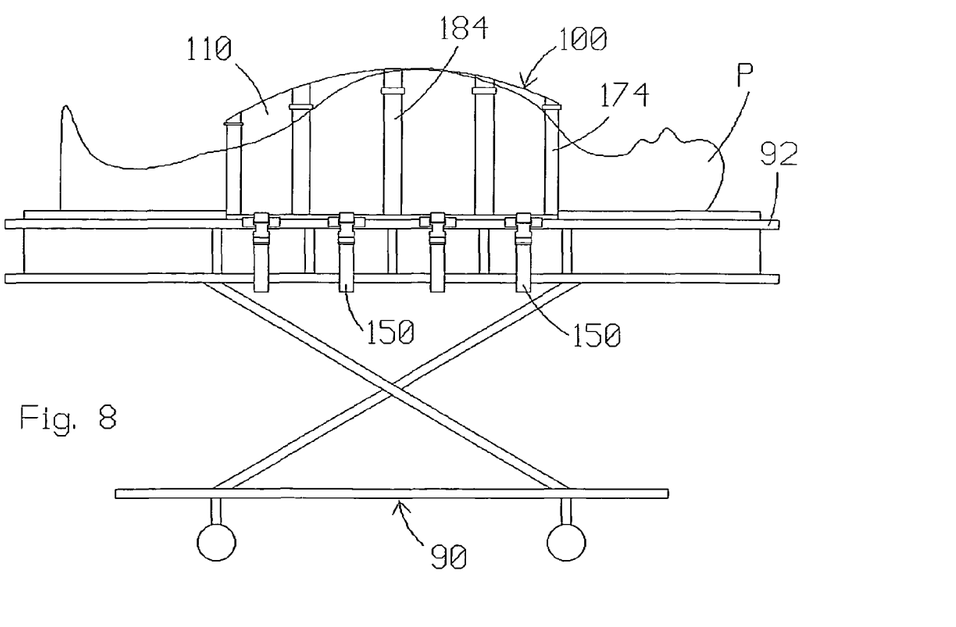
FIG. 8 is a side view of the patient restraining device wrapped and secured about the bariatric person of FIG. 7.

In a preferred application or method of use, the device 100 is positioned on top of the patient supporting structure 90 with the reinforcing straps 180 (and the patient restraining straps 184 and 185) extending perpendicular to the left side and the right side (as shown in FIG. 5). Then, the sheet of fabric 110 is fastened to the patient supporting structure 90. In this regard, the anchor straps 150 are secured about the left and right sides of the support structure (as shown in FIG. 8). A person P is positioned on top of the sheet of fabric 110 and the platform 91 (as shown in FIG. 7). Then the sheet of fabric 110 is wrapped about the person's torso, and the patient restraining straps 174,175 and 184,185 are secured about the sheet of fabric 110 and the person P, thereby safely and comfortably securing the person P to the patient supporting structure 90. In this regard, opposing straps 174 and 175 are adjusted and interconnected to snugly engage the person P, and opposing straps 184 and 185 are similarly adjusted and interconnected to snugly engage the person P (as shown in FIG. 8). Typically, the person's arms are kept outside the sheet of fabric 110. The device 100 restrains the person P in a manner that does not compromise breathing, and that typically lowers the anxiety of the person P.

The patient supporting structure 90 is sized and configured to safely support a person of a maximum size, and the person P is greater than that maximum size. More specifically, the person P has an excessively large abdominal section that makes direct placement on the cot 90 uncomfortable and potentially unsafe for both the person P and the personnel responsible for handling the cot 90. In this regard, the large abdominal mass M of the person P is capable of shifting significantly when the person P is positioned on the cot 90 without the device 100. Any such shift is capable of placing the person P in an awkward and potentially painful position, as well as tipping the cot 90 or putting significant strain on the people handling the cot 90. When implemented as shown in FIG. 8, the device 100 keeps the abdominal mass M over center relative to the cot 90, so the person P feels stable and secure, and the cot 90 remains stable and secure.

Figure 10:
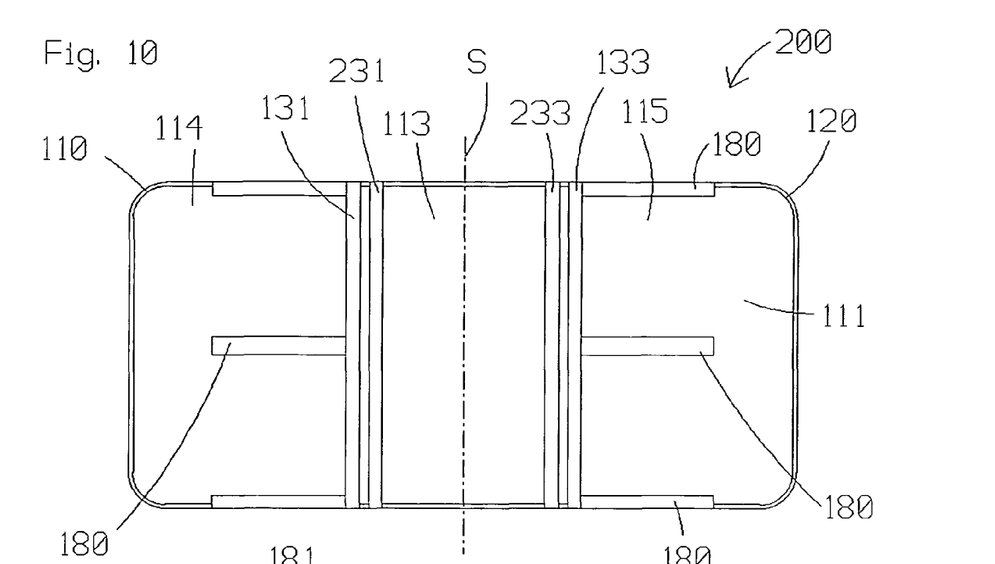
FIG. 10 shows an interior side of an alternative embodiment patient restraining device constructed according to the principles of the present invention.
Figure 11:
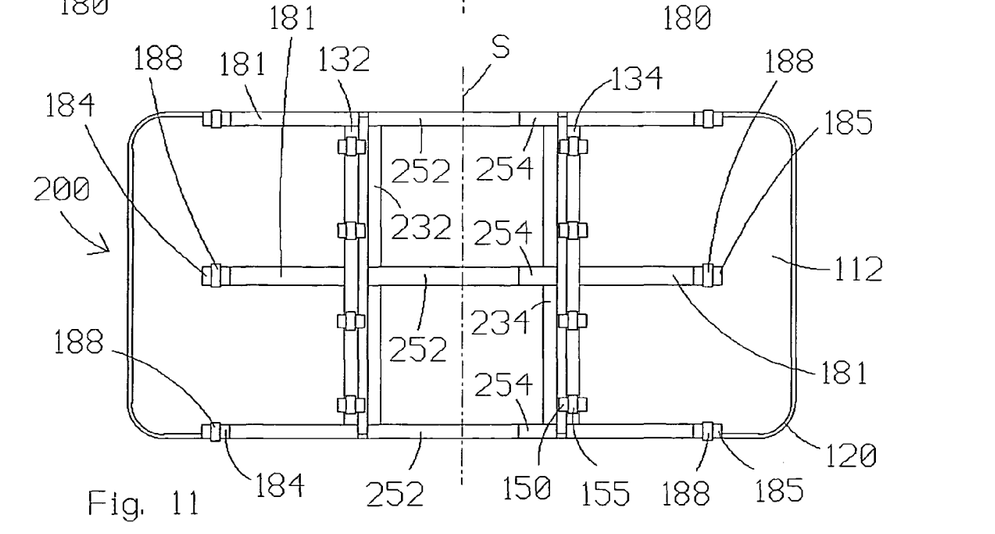
FIG. 11 shows an opposite, exterior side of the alternative embodiment patient restraining device of FIG. 1.

FIGS. 10-11 show another patient restraining device 200 constructed according to the principles of the present invention. As suggested by the common reference numerals, the device 200 is similar in many respects to the device 100 described with reference to FIGS. 1-9. Accordingly, the following description of the device 200 will focus primarily on the distinctions between the device 200 and the device 100.

The device 200 is configured for connection to a long board type of patient handling device, as well as an ambulance cot 90. In this regard, reinforcing straps 231 and 232 are disposed on respective first and second sides 111 and 112 of the sheet 110, inward from and parallel to the straps 131 and 132. The straps 231 and 232 are aligned with one another to extend laterally across the sheet 110, and the strap 231 is sewn to the strap 232 with the sheet 110 secured therebetween. Similarly, reinforcing straps 233 and 234 are disposed on respective first and second sides 111 and 112 of the sheet 110, inward from and parallel to the straps 133 and 134. The straps 233 and 234 are aligned with one another to extend laterally across the sheet 110, and the strap 233 is sewn to the strap 234 with the sheet 110 secured therebetween. Three "hook-type" fastening straps 252 are sewn to respective portions of the reinforcing strap 232, and three "loop-type" fastening straps 254 are sewn to respective portions of the reinforcing strap 234. The straps 252 are releasably connected to respective straps 254 to secure a long board type of patient handling device between the straps 252 and 254 and the central portion 113 of the device 200.

The "bundled" anchor straps 150 are arranged to fall outside the perimeter or sidewalls of the long board device. As described above with reference to the device 100, the anchor straps 150 are operable to secure the device 200 to an ambulance cot 90. In this alternative mode of operation, the long board straps 252 and 254 lie substantially flat beneath the patient.

Three patient restraining straps or connectors 184 are connected to the first end section 114 of the sheet of fabric 100. Similarly, three patient restraining straps or connectors 185 are connected to the second end section 115 of the sheet of fabric 110. Each patient restraining strap 184 and 185 may be described in terms of (1) a first portion that, together with a corresponding, opposite side strap 180, is secured to the sheet of fabric 110 like the reinforcing straps 131-134, and a second portion that is a loose end; or alternatively, (2) just loose portions that are connected to the distal ends of respective reinforcing straps 181. In any event, each reinforcing strap 180 has a first end that is retained between respective reinforcing straps 131-134, and extends longitudinally one foot from respective reinforcing straps 131-134 to an opposite, second end.

The present invention may also be described in terms of various methods, including, for example, a method of restraining a patient relative to a patient supporting structure. Such a method may involve the steps of providing a patient supporting structure having a platform that extends longitudinally from a head end to a foot end, and laterally from a left side to a right side; providing a restraining device having a sheet of fabric and connector straps secured to the sheet of fabric; positioning the device on top of the platform with the connector straps extending perpendicular to the sides; fastening the sheet of fabric to the patient supporting structure; positioning a person on top of the sheet of fabric and the platform; wrapping the sheet of fabric about the person; and securing the connector straps about the sheet of fabric and the person to safely and comfortably securing the person to the patient supporting structure. Additional steps may involve essentially reversing several of the foregoing steps, including, for example, releasing the connector straps; unwrapping the sheet of fabric; removing the person from the sheet of fabric and the platform; and removing the sheet of fabric from the patient supporting structure. Other additional steps may involve positioning a relatively smaller person on the patient supporting structure without using the restraining device; removing the relatively smaller person from the platform; and repeating the initial method steps with the same restraining device and a third, relatively larger person. In other words, the restraining device may be used repeatedly and intermittently depending on the needs of individual patients to be transported.

Multiple embodiments of the present invention have been disclosed with the understanding that additional embodiments may be derived from this disclosure without departing from the scope of the present invention. For example, with the exception of complementary buckle members, the device 100 is symmetrical about a center line S, but the present invention is not limited to such an arrangement. On an alternative embodiment, the fabric may be arranged to extend from only one side of the patient supporting structure, and to be secured to the opposing side by any of the methods disclosed herein, or by suitable alternative methods.

In conclusion, recognizing that this disclosure will enable persons skilled in the art to derive various modifications, improvements, and/or applications that nonetheless embody the essence of the invention, the scope of the present invention is to be limited only to the extent of the following claims.

What is claimed is:

1. A restraining device in combination with a patient supporting structure, the combination comprising:
   a patient supporting structure having a platform that extends longitudinally from a head end to a foot end, and laterally from a left side to a right side; and
   a restraining device, wherein the restraining device includes a sheet of fabric disposed on top of the patient supporting structure; fasteners interconnected between the sheet of fabric and the patient supporting structure; first reinforcement straps are disposed on a first side of the sheet of fabric, and second reinforcement straps are disposed on an opposite, second side of the sheet of fabric and aligned with respective said first reinforcement straps, and the first reinforcement straps are secured to respective said second reinforcement straps with the sheet of fabric secured therebetween; and connector straps secured to the sheet of fabric and selectively secured about the sheet of fabric and a person lying supine on the platform to wrap the person in the sheet of fabric and thereby safely and comfortably secure the person to the platform.

2. The combination of claim 1, wherein the patient supporting structure is an ambulance cot.

3. The combination of claim 1, wherein the fasteners include left side fasteners that are secured to a left one of the reinforcement straps, and right side fasteners that are secured to a right one of the reinforcement straps.

4. The combination of claim 3, wherein the left side fasteners are releasably secured in closed loops about respective portions of the left side of the platform, and the right side fasteners are releasably secured in closed loops about respective portions of the right side of the platform.

5. The combination of claim 3, wherein the connector straps include left side connector straps that are secured to a left one of the reinforcement straps, and right side connector straps that are secured to a right one of the reinforcement straps.

6. The combination of claim 1, wherein the patient supporting structure is sized and configured to safely support a person of a first maximum size, and the restraining device is sized and configured to safely accommodate a person of a relatively greater, second maximum size.

7. The combination of claim 1, wherein the restraining device is removable from the patient supporting structure, washable, and reusable.

8. The combination of claim 1, wherein the restraining device is foldable into a compact configuration that occupies less than one cubic foot of space.

9. A patient restraining device for temporarily, safely, and comfortably limiting movement of a body portion of a human patient relative to a patient supporting structure, comprising:
- a sheet of fabric having a length that is measured longitudinally and a width that is measured laterally and perpendicular to the length;
- a first strap and a second strap disposed on respective first and second sides of the sheet, and aligned with one another to extend laterally across the sheet, wherein the first strap is secured to the second strap with the sheet secured therebetween;
- a third strap and a fourth strap disposed on respective first and second sides of the sheet, and aligned with one another to extend laterally across the sheet, wherein the third strap is secured to the fourth strap with the sheet secured therebetween, and the first strap and the second strap cooperate with the third strap and the fourth strap to divide the sheet into three sections, including a middle section, a first end section, and an opposite, second end section;
- fasteners configured and arranged for connecting the second strap and the fourth strap to the patient supporting structure;
- first end connectors secured to the first end section; and
- second end connectors secured to the second end section, wherein the second end connectors are selectively connected to respective said first end connectors to wrap the body portion within the fabric.

10. The patient restraining device of claim 9, wherein the patient supporting structure includes a back supporting platform, a left rail, left side posts that extend between the left rail and a left side of the platform, a right rail, and right side posts that extend between the right rail and an opposite, right side of the platform, and the fasteners include first fastener straps that are secured to the first strap and secured into loops about at least one of the left rail and the left side posts, and the fasteners include second fastener straps that are secured to the third strap and secured into loops about at least one of the right rail and the right side posts.

11. The patient restraining device of claim 10, wherein two first said fasteners are secured about the left rail on opposite sides of one of the left side posts, and two first said fasteners are secured about the left rail on opposite sides of another one of the left side posts, and two second said fasteners are secured about the right rail on opposite sides of one of the right side posts, and two second said fasteners are secured about the right rail on opposite sides of another one of the right side posts.

12. The patient restraining device of claim 10, wherein each of the fasteners includes mating first and second buckle members and a fastener strap extending therebetween.

13. The patient restraining device of claim 9, wherein each of the first end connectors includes a connector strap secured to the sheet of fabric, and a first buckle member secured to a distal end portion of a respective connector strap, and each of the second end connectors includes a connector strap secured to the sheet of fabric, and a mating, second buckle member secured to a distal end portion of a respective connector strap.

14. The patient restraining device of claim 13, wherein each said connector strap has an opposite end portion that is arranged to extend longitudinally, aligned with a respective, opposite side support strap, and secured to both the sheet of fabric and the respective, opposite side support strap.

15. The patient restraining device of claim 14, wherein each said connector strap has an intermediate portion that extends between the opposite end portion and a respective said buckle member, and each said intermediate portion is selectively adjustable in length.

16. A method of restraining a patient relative to a patient supporting structure, comprising the steps of:
- (a) providing a patient supporting structure having a platform that extends longitudinally from a head end to a foot end, and laterally from a left side to a right side;
- (b) after determining that the person is too large to be safely supported on the platform without performing steps (c)-(g), providing a restraining device having a sheet of fabric and connector straps secured to the sheet of fabric; and
- (c) positioning the device on top of the platform with the connector straps extending perpendicular to the left side and the right side; and
- (d) fastening the sheet of fabric to the patient supporting structure; and
- (e) positioning a person on top of the sheet of fabric and the platform; and
- (f) wrapping the sheet of fabric about the person; and
- (g) securing the connector straps about the sheet of fabric and the person, thereby safely and comfortably securing the person to the patient supporting structure.

17. The method of claim 16, further comprising the steps of (h) releasing the connector straps; (i) unwrapping the sheet of fabric; (j) removing the person from the sheet of fabric and the platform; and (k) removing the sheet of fabric from the patient supporting structure.

18. The method of claim 17, further comprising the steps of (l) laundering the restraining device; and then repeating steps (a)-(g) with the same restraining device and a different person.

19. The method of claim 17, further comprising the steps of (l) positioning a relatively smaller person on the patient supporting structure without using the restraining device; (m) removing the relatively smaller person from the platform; and (n) repeating steps (a)-(g) with the same restraining device and a third, relatively larger person.

20. The method of claim 16, wherein step (b) involves removing the restraining device from a storage bag.

21. The method of claim 16, wherein step (a) involves removing an ambulance cot from an emergency vehicle.

* * * * *